United States Patent

Kobashi

Patent Number: 5,428,993
Date of Patent: Jul. 4, 1995

[54] AUTOMATIC ANALYZER HAVING FUNCTION OF DETECTING REMAINING LIQUID QUANTITY

[75] Inventor: Masayuki Kobashi, Kobe, Japan

[73] Assignee: Toa Medical Electronics Co., Ltd., Kobe, Japan

[21] Appl. No.: 12,411

[22] Filed: Feb. 2, 1993

[30] Foreign Application Priority Data

Feb. 26, 1992 [JP] Japan .............. 4-018285 U

[51] Int. Cl.6 ............................................ B67D 5/14
[52] U.S. Cl. ................................. 73/149; 222/58
[58] Field of Search .................. 73/149, 296; 222/23, 222/52, 58; 436/180; 422/67, 68.1; 177/62, 68, 100, 103, 90; 137/403

[56] References Cited

U.S. PATENT DOCUMENTS

| | | | |
|---|---|---|---|
| 4,284,210 | 8/1981 | Horak | 222/23 |
| 4,483,927 | 11/1984 | Takekawa | 422/67 |
| 4,591,568 | 5/1986 | Banno et al. | 436/180 |
| 4,605,297 | 8/1986 | Livingston et al. | 222/58 |
| 4,777,832 | 10/1988 | Prodosmo et al. | 73/863.02 |
| 4,844,298 | 7/1989 | Ohoka et al. | 222/58 |
| 5,040,699 | 8/1991 | Gangemi | 222/58 |

*Primary Examiner*—Robert Raevis
*Attorney, Agent, or Firm*—Jones, Tullar & Cooper

[57] ABSTRACT

In an automatic analyzer, waste of specimens and reagents is prevented by having a function for detecting the remaining quantity of the liquids being used such as a reagent, a diluent liquid and a cleaning liquid. The weight data (m) of the reagent container only, and the gross weight data (M) of the reagent container and the reagent in the container are entered in an operation processor of the automatic analyzer, and the reagent remaining quantity (Q)=M-m in the reagent container is determined, while the required reagent quantity (D) necessary for specimen processing of the set specimens is determined, and by comparing the both (Q and D), it is judged whether or not to process the specimens.

4 Claims, 5 Drawing Sheets

AUTOMATIC ANALYZER HAVING FUNCTION OF DETECTING REMAINING LIQUID QUANTITY

BACKGROUND OF THE INVENTION

The present invention relates to an automatic analyzer having a function of detecting the remaining quantity of a liquid being used (reagent, diluent liquid, cleaning liquid, or the like).

In an automatic analyzer, liquids such as reagents and cleaning liquids are used. If these liquids are used up during measurement, not only can the measurement not be continued in such a state, but also the results of the measurement cannot obtained from the specimens in measured or the process of reaction. Generally, a spare liquid tank is incorporated in the analyzer so that the effect may not appear immediately if an external liquid tank becomes empty.

In some automatic analyzers, it takes a long time (more than scores of minutes) from sampling of the liquid specimen until the result of the measurement is produced. For example, it takes a long time in the reaction process between the liquid specimen and a reagent, or in the measurement process of the reaction liquid. The antigen-antibody reaction is one such example.

When treatment of one specimen requires a long time, treating processes of plural specimens are overlapped to improve processing capacity.

In the case of such an overlapped treatment, if the liquid is used up on the way, the apparatus stops. If refilling is attempted with a fresh liquid while stopped, bubbles are formed, which may cause a measuring error. Besides, if it is required to perform a reaction process in a specific condition, the reaction time varies and a correct result is not obtained. In particular, in the case of an immunity apparatus, the reaction process is conducted in severe conditions in specific circumstances. Accordingly, if one runs out of the liquid in the midst of the operation, all specimens in the treatment process are wasted, and the operation must be started from the beginning, which means an increase in the running cost and loss of time.

Hitherto, the operator checked the remaining quantity of reagents and other liquid before starting a measurement, and replaced the liquid with new liquid if it was estimated to run short in the midst of the operation. Of course, the liquid may be replenished during measurement, but bubbles may be formed and a measuring error may result.

It is, however, bothersome to check the remaining liquid quantity, and problems were often caused when forgetting to check or mispredicting the remainder.

OBJECT AND SUMMARY OF THE INVENTION

It is hence a primary object of the present invention to provide an automatic analyzer capable of detecting the remaining quantity of a liquid such as a reagent in a reagent container attached (installed) to the automatic analyzer, and prohibiting start of treatment of a new specimen when a liquid shortage is anticipated, thereby eliminating specimen and reagent waste.

It is another object of the present invention to provide an automatic analyzer for automatically changing over to another reagent container when the liquid is insufficient in a reagent container, so that it is not necessary to stop the measurement.

To achieve the above objects, the automatic analyzer has the function of detecting remaining liquid quantity as explained by reference to FIG. 1 and FIG. 2. The automatic analyzer comprises a reagent container 12 attached (installed) to an automatic analyzer 10, and a weight sensor 16 for measuring the weight of the reagent container by mounting the reagent container 12 thereon, memory means 20 for storing weight data m of the reagent container 12 itself, remaining quantity calculating means 22 for determining the remaining quantity $Q=M-m$ in the reagent container 12 from the weight data M obtained from the weight sensor 16 and the weight data m of the reagent container 12, setting means 24 for setting measuring items for each specimen, required quantity calculating means 26 for determining the reagent required quantity D for the specimen set in the setting means 24, judging means 28 for comparing the reagent remaining quantity Q determined by the remaining quantity calculating means 22 and the reagent required quantity D determined by the required quantity calculating means 26, and judging approval or disapproval of the processing (treating) of the specimen, and display means 30 for displaying the approval or disapproval of the specimen processing on the basis of the judgement result W of the judging means 28.

The reagent container 12 is provided either inside or outside of the automatic analyzer 10.

Besides, the remaining quantity calculating means 22, required quantity calculating means 26, and judging means 28 may be constructed in one operation processor 21, so that the functions of the remaining quantity calculating means 22, required quantity calculating means 26, and judging means 28 may be exhibited by one operation processor 21.

The weight data m of the reagent container 12 only, and the gross weight data M of the reagent container 12 and the reagent in the container are fed into the operation processor 21 of the automatic analyzer 10, and the reagent remaining quantity $Q=M-m$ in the reagent container 12 is determined, while the reagent quantity D necessary for specimen processing (treating) as for the specimen set in the setting means 24 is determined, and by comparing both (Q and D) in the judging means 28, it is judged whether the specimen may be processed (treated) or not.

Figure 3:
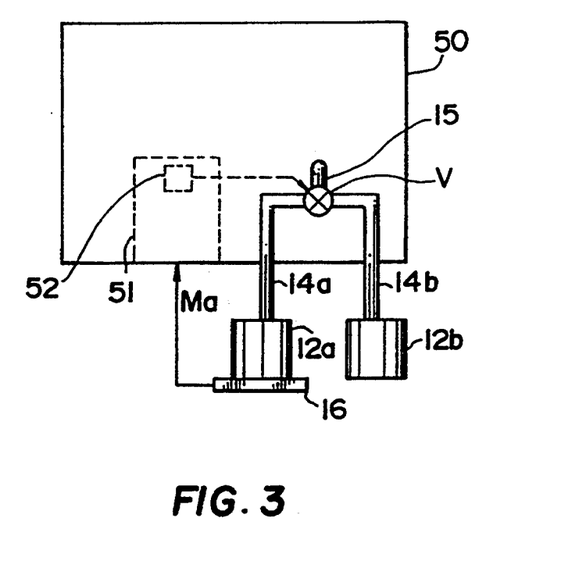
FIG. 3 is a schematic view showing another embodiment of an automatic analyzer of the present invention.
Figure 4:
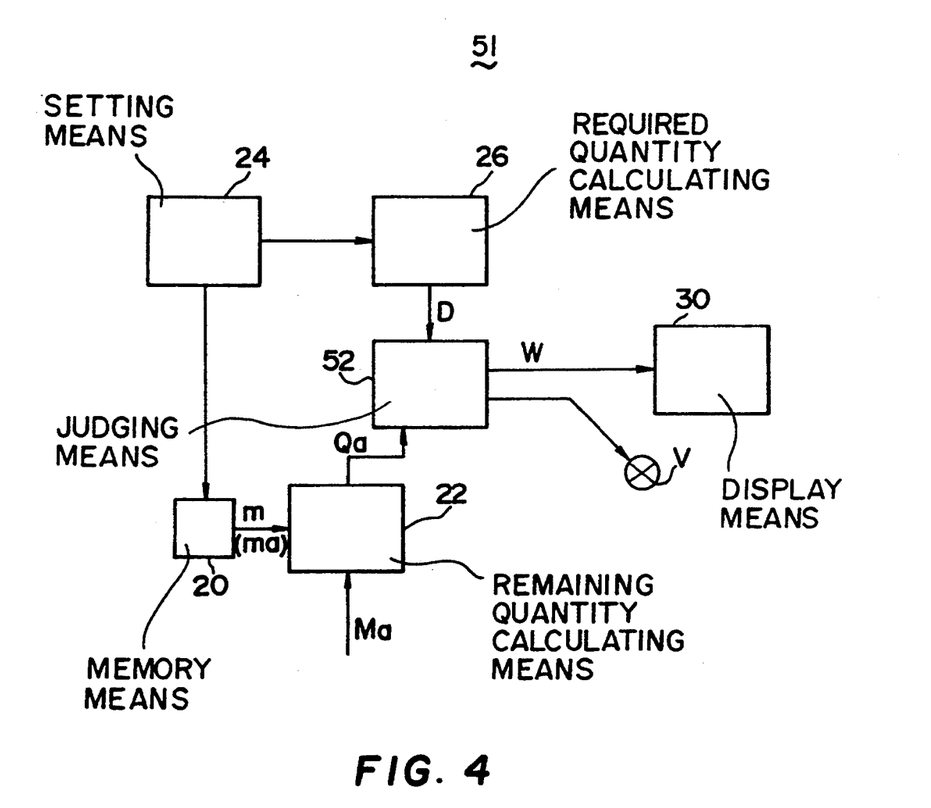
FIG. 4 is a block diagram showing an example of a remaining liquid quantity detector incorporated in the automatic analyzer shown in FIG. 3.

Another apparatus of the present invention is, for example, that shown in FIG. 3 and FIG. 4, which show an automatic analyzer comprising a main reagent container 12a and a sub (supplementary) reagent container 12b connected to an automatic analyzer 50 through a valve V, and a weight sensor 16 for measuring the weight of the main reagent container 12a by mounting it thereon. This apparatus further comprises:

memory means 20 for storing the weight data ma of the main reagent container 12a itself, remaining quantity calculating means 22 for determining the remaining quantity $Qa=Ma-ma$ in the main reagent container 12a from the weight data Ma obtained from the weight sensor 16 and the weight data ma of the main reagent container 12a, setting means 24 for setting measuring items for each specimen, required quantity calculating means 26 for determining the reagent required quantity D for the specimen set in the setting means 24, judging means 52 for comparing the reagent remaining quantity Qa determined by the remaining quantity calculating means 22 and the reagent required quantity D determined by the required quantity calculating means 26, and judging an approval or disapproval for processing of the specimen, and display means 30 for displaying the approval or disapproval of specimen processing on the basis of the judgement result W of the judging means 52.

In the judging means 52, when the reagent remaining quantity Qa is enough, the reagent from the main reagent container 12a is used, and when the reagent remaining quantity Qa is not enough, the valve V is changed over and controlled to use the reagent from the sub reagent container 12b temporarily.

Besides, the remaining quantity calculating means 22, required quantity calculating means 26, and judging means 52 may be constructed as one operation processor, so that the functions of the remaining quantity calculating means 22, required quantity calculating means 26, and judging means 52 may be embodied in one operation processor.

Figure 5:
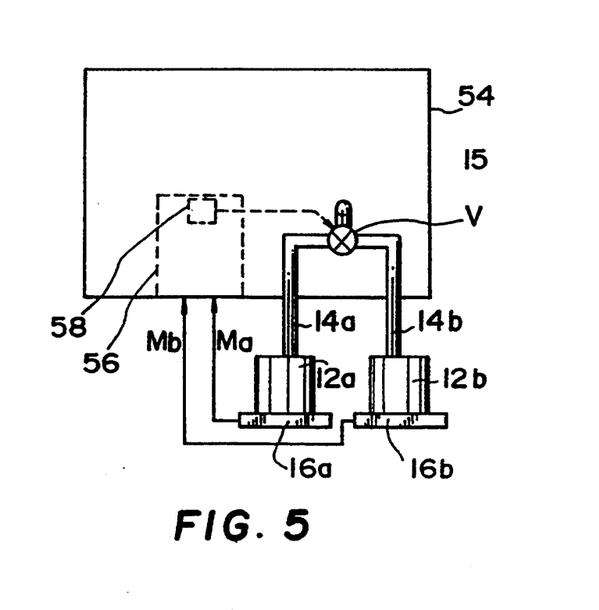
FIG. 5 is a schematic view showing another embodiment of an automatic analyzer of the present invention.
Figure 6:
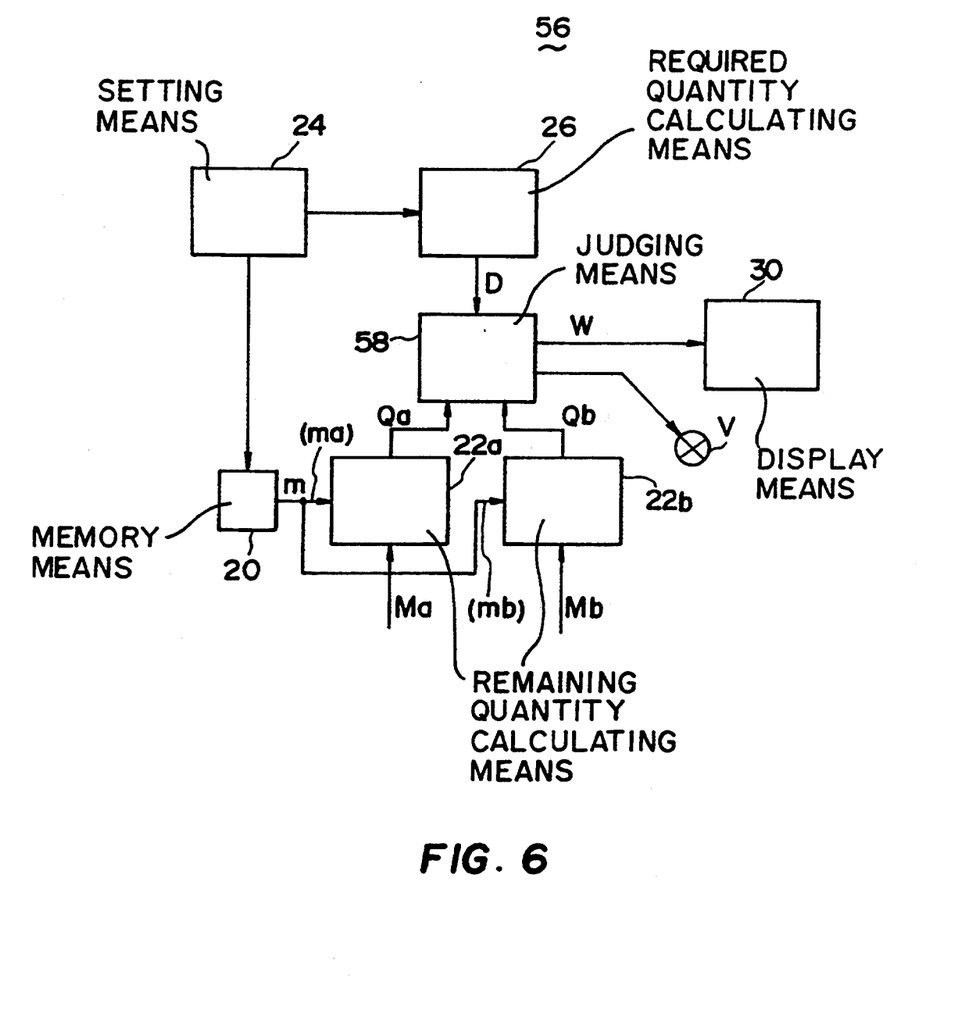
FIG. 6 is a block diagram showing an example of a remaining liquid quantity detector incorporated in the automatic analyzer shown in FIG. 5.
Figure 7:
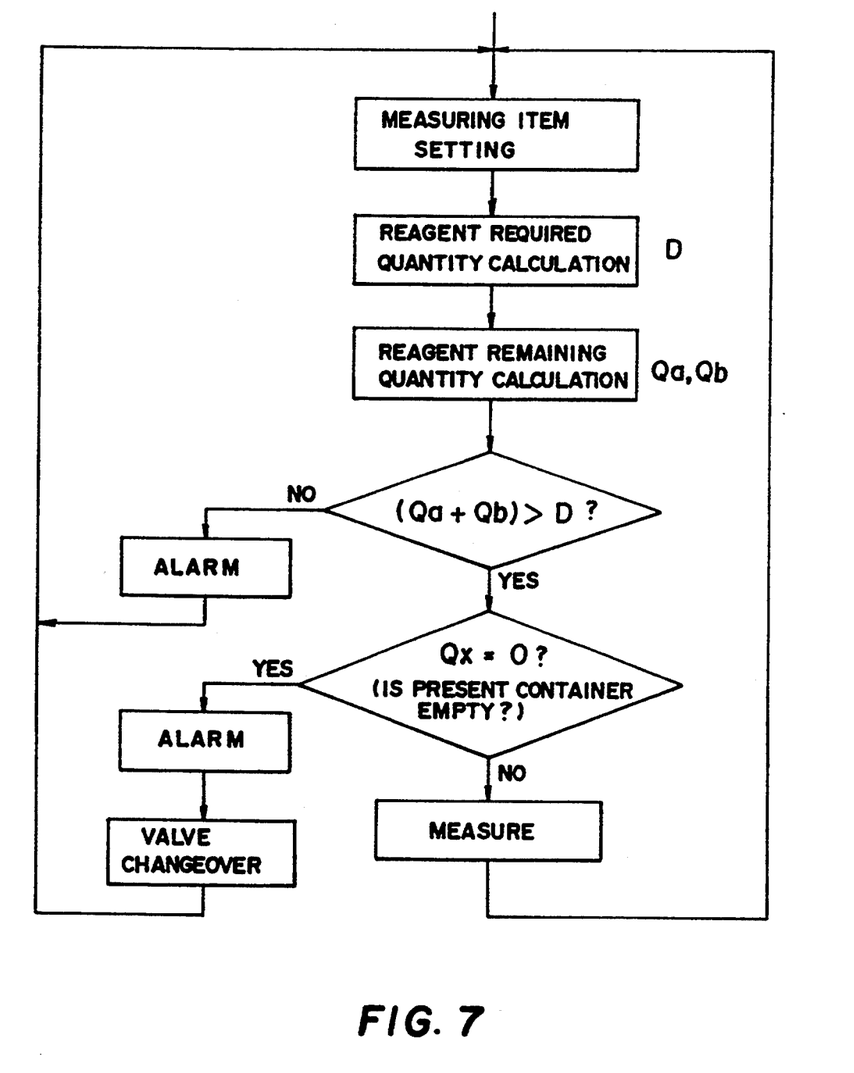
FIG. 7 is a flow chart for the automatic analyzer shown in FIG. 5.

Another apparatus of the present invention is, for example, that shown in FIG. 5 through FIG. 7, which show an automatic analyzer comprising a main reagent container 12a and sub reagent container 12b connected to an automatic analyzer 54 through a valve V, and weight sensors 16a, 16b for measuring the weights of the reagent containers by mounting the main reagent containers 12a on weight sensor 16a and the sub reagent container 12b on weight sensor 16b. This apparatus further comprises:

memory means 20 for storing the weight data ma, mb of both the reagent containers 12a, 12b, remaining quantity calculating means 22a for determining the remaining quantity Qa=Ma-ma in the main reagent container 12a from the weight data Ma obtained from the weight sensor 16a and the weight data ma of the main reagent container 12a, remaining quantity calculating means 22b for determining the remaining quantity Qb=Mb-mb in the sub reagent container 12b from the weight data Mb obtained from the weight sensor 16b and the weight data mb of the sub reagent container 12b, setting means 24 for setting measuring items for each specimen, required quantity calculating means 26 for determining the reagent required quantity D for the specimen set in the setting means 24, judging means 58 for comparing the reagent remaining quantities Qa, Qb determined by the remaining quantity calculating means 22a, 22b and the reagent required quantity D determined by the required quantity calculating means 26, and judging an approval or disapproval for processing of the specimen, and display means 30 for displaying the approval or disapproval of specimen processing on the basis of the judgement result W of the judging means 58.

In the judging means 58, when the reagent remaining quantity Qa or Qb in one reagent container 12a or 12b is not enough, the valve V is changed over and controlled to use the reagent from the other reagent container 12b or 12a temporarily.

Besides, the remaining quantity calculating means 22a, 22b, required quantity calculating means 26, and judging means 58 may be constructed as one operation processor, so that the functions of the remaining quantity calculating means 22a, 22b, required quantity calculating means 26, and judging means 58 may be embodied in one operation processor.

Incidentally, when the weight of the main reagent container 12a and the weight of the sub reagent container 12b are equal, the weight data are ma=mb, and hence the data of only one weight m may be used.

DETAILED DESCRIPTION OF THE PREFERRED EMBODIMENTS

Referring now to the drawings, some of the preferred embodiments of the present invention are described in detail below.

Figure 1:
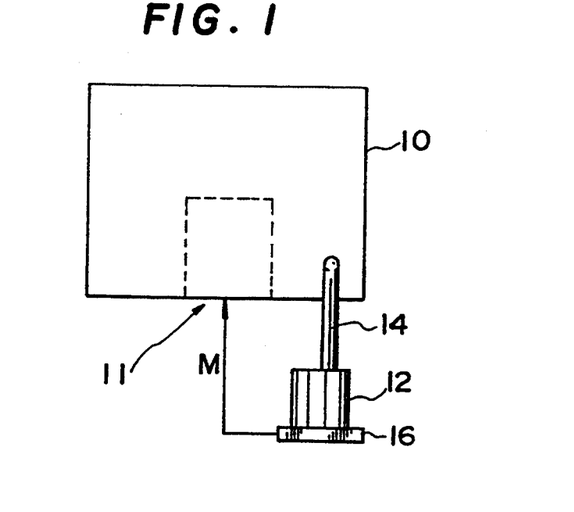
FIG. 1 is a schematic view showing an embodiment of an automatic analyzer of the present invention.

FIG. 1 shows an embodiment of an automatic sample analyzer of the present invention. The sample analyzer is specifically, for example, an immunoagglutination measuring apparatus for measuring trace protein in human serum by the CIA method (counting immunoassay). Plural reagents are used in the immunoagglutination measuring apparatus. For example, a latex reagent for extracorporeal diagnosis, buffer solution, sheath liquid, and cleaning liquid are used. Of them, the latex reagent and buffer solution are controlled in temperature and accommodated within the analyzer. The sheath liquid and cleaning liquid, of which temperature control is not necessary, are installed outside the analyzer. Of course, they may be incorporated within the analyzer. Plural external reagents may be connected to the analyzer, but they are represented by one reagent in FIG. 1.

Figure 2:
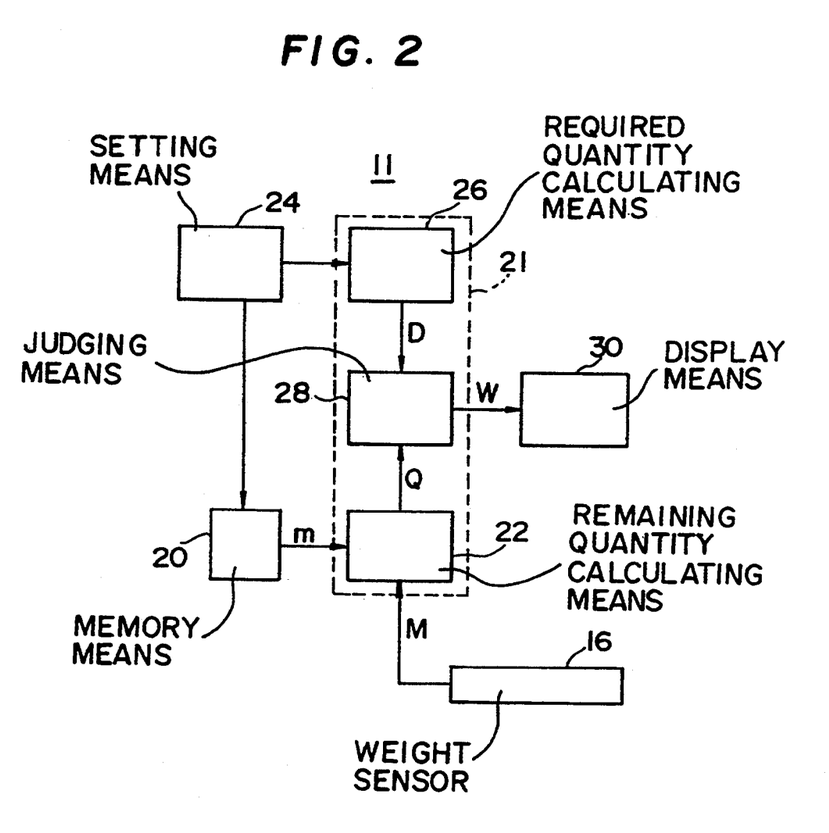
FIG. 2 is a block diagram showing an example of a remaining liquid quantity detector incorporated in the automatic analyzer shown in FIG. 1.

FIG. 2 is a block diagram showing an example of a remaining liquid quantity detector 11 provided in the automatic analyzer 10.

As shown in FIG. 1, the reagent container 12 containing the reagent is connected to the analyzer 10 through a tube 14, and is put on a weight sensor 16. From the weight sensor 16 to the analyzer 10, the gross weight data M of the reagent container 12 and the reagent in the container is transmitted. On the other hand, in FIG. 2, in memory means 20, the weight data m (empty weight) of the container only of the reagent container 12 is stored. The measuring items for each specimen is set in setting means 24. An operation processor 21 of the automatic analyzer 10 receives these pieces of information, and determines the remaining reagent quantity Q=M-m in the reagent container 12, and also determines the reagent quantity D necessary for specimen processing (treating) for the set specimen, and compares them to judge whether to process (treat) the specimen or riot. A display of the reagent remaining quantity and a liquid shortage alarm are shown in display means 30.

A judgement is made before starting a measurement, and when judged to be short of liquid, processing of the specimen is not started.

The operation processor 21 comprises, for example, remaining quantity calculating means 22, required quantity calculating means 26, and judging means 28. The remaining quantity calculating means 22 possesses a function of calculating the remaining quantity $Q=M-m$ in the reagent container 12 from the weight data M obtained from the weight sensor 16 and the empty weight data m of the reagent container 12, the required quantity calculating means 26 possesses a function of calculating the reagent required quantity D for the specimen set in the setting means 24, and the judging means 28 possesses a function of comparing the reagent remaining quantity Q calculated in the remaining quantity calculating means 22 and the reagent required quantity D calculated in the required quantity calculating means 26, and judging an approval or disapproval for processing of the specimen.

Table 1 explains the setting means 24, showing the screen of the display unit of the analyzer 10 in the item setting mode. In this item setting mode, the measuring items can be specified (designated) for each specimen.

TABLE 1

| Rack No. | Specimen No. | AFP | CEA | FRN | CA19-9 |
|---|---|---|---|---|---|
| 1-1 | 0001 | * | * | | |
| 1-2 | 0002 | * | * | | |
| 1-3 | 0003 | * | * | * | |
| 1-4 | 0004 | | | * | * |
| 1-5 | 0005 | * | | * | * |
| 2-1 | 0006 | * | * | | |
| 2-2 | 0007 | | * | | |
| 2-3 | 0008 | | * | | |
| 2-4 | 0009 | | | * | |
| 2-5 | 0010 | * | | * | * |
| E3-1 | 1001 | * | | | |
| E3-2 | 1002 | * | | | * |

Reagent remaining quantity: 9 tests

In Table 1, AFP, CEA, FRN, CA 19-9 are names of items. The rack No. indicates the specimen accommodating position. In this embodiment, five specimens are accommodated in one rack. Items are specified by entering the measuring item specifying mark of "*" in the column of the item to be measured while entering the rack No. and specimen No. The input is made by input keys. Items not required to be measured are kept blank.

At the bottom of Table 1, "Reagent remaining quantity: 9 tests" indicates that the remainder is enough for nine more tests. The number of tests is the number of measuring items. In Table 1, the number is indicated by the * marks, and 23 tests are registered (shown) in total. Supposing the reagent consumption per item to be K in all items, and assuming:

reagent gross weight M
reagent container weight m
reagent remaining quantity Q ($=M-m$)
the number of tests that can be measured is expressed as $T=Q/K$.

In the rack No. column, the printed "E" mark indicates an emergency specimen. The specimen with this emergency specimen mark must be measured in the first place. That is, specimens in rack Nos. 3-1, 3-2 (emergency specimen group) have a higher priority than the specimens in other racks (ordinary specimen group). Between the same emergency specimens, the priority is the same, but the specimen with the earlier number has the greater priority in this case. Therefore, the priority order in Table 1 is in the sequence of rack Nos. 3-1, 3-2, 1-1, 1-2, 1-3, 1-4, 1-5, 2-1, 2-2, 2-3, 2-4, and 2-5.

Thus, after setting of the necessary items, approval or disapproval for processing of specimen is judged.

Table 2 shows the display screen after judgement for approval or disapproval of specimen processing.

TABLE 2

| Rack No. | Specimen No. | AFP | CEA | FRN | CA19-9 |
|---|---|---|---|---|---|
| 1-1 | 0001 | ○ | ○ | | |
| 1-2 | 0002 | ○ | ○ | | |
| 1-3 | 0003 | * | * | * | |
| 1-4 | 0004 | | | * | * |
| 1-5 | 0005 | * | | * | * |
| 2-1 | 0006 | * | * | | |
| 2-2 | 0007 | | * | | |
| 2-3 | 0008 | | * | | |
| 2-4 | 0009 | | | * | |
| 2-5 | 0010 | * | | * | * |
| E3-1 | 1001 | ○ | | | |
| E3-2 | 1002 | ○ | | | ○ |

Reagent remaining quantity: 9 tests

A change from a "*" mark to a "o" mark in the item specifying column indicates an item that can be measured as an estimate from the reagent remaining quantity. It is, so to speak, a measurement enable mark. Calculating the number of tests Ti in each specimen i from the highest rank of priority, it requires $T1+T2+T3+T4=1+2+2+2=7$ in up to specimen numbers 1001, 1002, 0001, 0002. Up to 0003, it requires $T1+T2+T3+T4+T5=1+2+2+2+3=10$. Seeing that $T1+\ldots+T4\,(=7)<T\,(=9)<T1+\ldots+T5\,(=10)$, it is possible to measure specimens $i=1$ to 4, that is, specimen numbers 1001, 1002, 0001, and 0002.

Depending on the case, moreover, individually calculating the total number of tests Te in the emergency specimen group and the total number of tests Tu in the ordinary specimen group, when $Te<T<Tu$, only the emergency specimen group is measured, and the ordinary specimen group is not measured. Of course, when Te, $Tu<T$, both groups are measured.

Thus, the number of tests and the reagent quantity are correlated, and the relationship may be expressed in another way. That is, calculating the reagent required quantity Di in each specimen i from the highest rank of priority, it requires $D1+D2+D3+D4$ in up to specimen numbers 1001, 1002, 0001, 0002. Up to 0003, it requires $D1+D2+D3+D4+D5$. Seeing that $D1+\ldots D4<Q<D1+\ldots D5$, it is possible to measure specimens $i=1$ to 4, that is, specimen numbers 1001, 1002, 0001, and 0002.

Depending on the case, moreover, individually calculating the total reagent required quantity De in the emergency specimen group and the total reagent required quantity Du in the ordinary specimen group, when $De<Q<Du$, only the emergency specimen group is measured, and the ordinary specimen group is not measured. Of course, when De, $Du<Q$, both groups are measured.

Summing up, the cases may be classified as follows.

(1) The reagent required quantity data Di is determined for each set specimen i, the sum of products $\Sigma Di$ is calculated in the sequence from the specimen of the highest rank of priority, and specimens are measured up to specimen p satisfying the relationship $\Sigma Di<Q$.

(2) Specimens are divided into plural groups j differing in the priority. The reagent required quantity data Di is determined for each specimen i, the sum of products ΣDi is calculated in the sequence from the specimen of the highest priority, and specimens are processed up to specimen group r satisfying the relationship ΣDi<Q.

(3) The reagent required quantity data Di is determined for each set specimen i, and when the sum DT satisfies DT<Q, the specimens can be processed.

Besides, on the basis of the results of these judgements, messages such as "the reagent quantity is insufficient" and "start to measure emergency specimens 1001 to 1002 and ordinary specimens 0001 to 0002" may be displayed. Once the measurement is started, the result of a measurement is sequentially shown in the display unit.

Incidentally, reagent containers of different volumes may be used. When the container volume differs, the weight data m of the container itself varies, and in such a case it is necessary to judge the remaining liquid quantity by using the weight data m corresponding to the volume of the reagent containers. It is preferred, in such a case, to store the weight data of plural reagent containers to be used in the memory means 20, and set the type of the reagent container in the setting means 24, so that the weight data corresponding to the container can be selectively used. Otherwise, the weight data m may be directly written into the memory means 20 from the setting means 24. Besides, without setting the type of container in the setting means 24, it is also possible to judge the type of the container from the difference of the gross weight M of the reagent container.

Explained so far is a case of using one reagent container for one kind of reagent. In this manner, if the reagent remaining quantity is insufficient, it can be detected before running out of the liquid. However, until the reagent shortage is resolved, the analyzer remains stopped, and measurement halts (stops).

Accordingly, as shown in FIG. 3 and FIG. 4, in addition to the main reagent container 12a, a sub (supplementary) reagent container 12b is used, and when the reagent remaining quantity Qa in the main reagent container 12a becomes zero is therefore unusable, a valve V is changed over by a control signal from judging means 52 of a remaining quantity detector 51, and the reagent in the sub reagent container 12b is used, so that it is not necessary to stop the measurement if the liquid runs short in the main reagent container. That is, while the main reagent container 12a is being replaced with a new container, the reagent from the sub reagent container 12b can be used. When the main reagent container is changed, the reagent remaining quantity is sufficient, the valve is changed over to the initial state, and the reagent from the main reagent container 12a is used. The valve V possesses the state of communicating between a tube 14a and a tube 15, and a state of communicating between a tube 14b and the tube 15.

FIG. 5 shows an apparatus adding a sub weight sensor 16b for measuring the weight of the sub reagent container 12b further to the apparatus shown in FIG. 3.

FIG. 6 is a block diagram showing an example of the remaining quantity detector 56 in FIG. 5. It is supposed, meanwhile, that the weight of the main reagent container 12a and the weight of the sub reagent container 12b be equal to each other, that is, the same weight data m is used. FIG. 7 is a flow chart. The remaining quantity calculating means 22a, 22b calculate as follows:

$$Qa = Ma - m, \quad Qb = Mb - m.$$

The judging means 58 possesses a function of judging an approval or disapproval for specimen processing, and changing over the valve V, from the reagent remaining quantity Qa in the main reagent container 12a, the reagent remaining quantity Qb in the sub reagent container 12b, and the reagent required quantity D. Besides, corresponding to the reagent containers 12a, 12b, the weight data ma, mb of the reagent containers are stored in the memory means 20, and the operations of Qa=Ma-mb, Qb=Mb-mb may be calculated in the remaining quantity calculating means 22a, 22b, respectively.

Referring then to FIG. 7, the processing (treating) is explained below. Suppose the main reagent container 12a is being used, and that its remaining quantity Qa is short.

First, the sum of the reagent remaining quantities (Qa+Qb) and the reagent required quantity D are compared, and if the sum (Qa+Qb) is smaller, an alarm is issued. At this time, measurement is disabled.

When the sum (Qa+Qb) is greater than the reagent required quantity D, measurement is enabled. Next it is judged whether the remaining quantity Qx in the container being used at the present (in this case, the remaining quantity Qa in the main reagent container) has become zero or not. Unless the main reagent container 12a is empty, the measurement continues without changing over the valve. If the main reagent container 12a becomes empty, an alarm is issued, and the valve V is changed over at the same time. That is, the sub reagent container 12b is used. Examples of an alarm may include, among others, "Short of reagent" and "Decrease measuring items."

Being thus constructed, the present invention brings about the following effects.

(1) The reagent weight is measured, and this weight is compared with the required quantity of reagent calculated from the measuring items of the set specimens, the specimen processing is controlled accordingly, and therefore shortage of liquid in the midst of processing may be avoided. Hence, waste of specimen and reagent may be prevented, and re-measurement (re-inspection) is not required.

(2) Specimen processing may be done either in each specimen or in a specimen group, which is very efficient.

(3) When the liquid runs short in the main reagent container, it is automatically changed over to the sub reagent container, so that it is not necessary to interrupt (stop) the measurement.

Having described preferred embodiments of the present invention with the reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. An automatic analyzer for detecting a remaining liquid quantity, comprising;
   a main reagent container and sub reagent container;
   a valve connecting the two reagent containers;
   a weight sensor for measuring the weight of the reagent container by mounting the main reagent container thereon;
   memory means for storing the weight data (ma) of the empty main reagent container;

remaining quantity calculating means for determining the remaining quantity (Qa)=Ma-ma in the main reagent container from the weight data (Ma) obtained from the weight sensor and the weight data (ma) of the main reagent container;

setting means for setting measuring items for each specimen;

required quantity calculating means for determining a reagent required quantity (D) for the specimen set in the setting means;

judging means for comparing the reagent remaining quantity (Qa) determined by the remaining quantity calculating means and the reagent required quantity (D) determined by the required quantity calculating means, and judging an approval or disapproval for treating of the specimen in the form of a judgement result (W); and display means for displaying the approval or disapproval of specimen treating on the basis of the judgement result (W) of the judging means, wherein the reagent from the main reagent container is used when the judging means determines that the reagent remaining quantity (Qa) is enough, and the valve is changed over and controlled to temporarily use the reagent from the sub reagent container when the judging means determines that the reagent remaining quantity (Qa) is not enough.

2. The automatic analyzer according to claim 1, wherein the remaining quantity calculating means, the required quantity calculating means, and the judging means form a single operation processor.

3. An automatic analyzer for detecting remaining liquid quantity, comprising;

a main reagent container and sub reagent container;
a valve connecting the two reagent containers;

weight sensors for measuring the weights of the main and sub reagent containers respectively;

memory means for storing the weight data (ma), (mb) of both empty reagent containers;

remaining quantity calculating means for determining the remaining quantity (Qa)=Ma-ma in the main reagent container from the weight data (Ma) obtained from the weight sensor and the weight data (ma) of the main reagent container;

remaining quantity calculating means for determining the remaining quantity (Qb)=Mb-mb in the sub reagent container from the weight data (Mb) obtained from the weight sensor and the weight data (mb) of the sub reagent container;

setting means for setting measuring items for each specimen;

required quantity calculating means for determining a reagent required quantity (D) for the specimen set in the setting means;

judging means for comparing the reagent remaining quantities (Qa), (Qb) determined by the remaining quantity calculating means and the reagent required quantity (D) determined by the required quantity calculating means, and judging an approval or disapproval for treating of the specimen in the form of a judgement result (W); and display means or displaying the approval or disapproval of specimen treating on the basis of the judgement result (W) of the judging means, wherein when the reagent remaining quantity (Qa) or (Qb) in one reagent container is not enough, the valve is changed over and controlled to temporarily use the reagent from the other reagent container.

4. The automatic analyzer according to claim 3, wherein the remaining quantity calculating means, the required quantity calculating means, and the judging means form a single operation processor.

* * * * *